United States Patent
Aoshima et al.

[11] Patent Number: 6,099,478
[45] Date of Patent: Aug. 8, 2000

[54] PULSE COUNTER AND PULSE DISPLAY METHOD

[75] Inventors: Ichiro Aoshima; Tsukasa Kosuda, both of Suwa, Japan

[73] Assignees: Seiko Epson Corporation, Tokyo; Seiko Instruments, Inc., Chiba, both of Japan

[21] Appl. No.: 09/180,727

[22] PCT Filed: Mar. 18, 1998

[86] PCT No.: PCT/JP98/01142

§ 371 Date: Nov. 12, 1998

§ 102(e) Date: Nov. 12, 1998

[87] PCT Pub. No.: WO98/41142

PCT Pub. Date: Sep. 24, 1998

[30] Foreign Application Priority Data

Mar. 18, 1997 [JP] Japan ................................. 9-064991

[51] Int. Cl.[7] .................................................. A61B 5/02
[52] U.S. Cl. .................................... 600/500; 600/502
[58] Field of Search ................................. 600/500, 502, 600/503, 501, 481

[56] References Cited

U.S. PATENT DOCUMENTS 5,697,374  12/1997  Odagiri et al. ........................ 600/500
5,795,300   8/1998  Bryars et al. ......................... 600/500
5,807,267   9/1998  Bryars et al. ......................... 600/500

FOREIGN PATENT DOCUMENTS

| | | |
|---|---|---|
| 60-259239 | 12/1985 | Japan . |
| 4-75503 | 7/1992 | Japan . |
| 6-245912 | 9/1994 | Japan . |
| 7-148127 | 6/1995 | Japan . |
| 7-227383 | 8/1995 | Japan . |
| 8-289876 | 11/1996 | Japan . |

*Primary Examiner*—Cary O'Connor
*Assistant Examiner*—Navin Natnithithadha
*Attorney, Agent, or Firm*—Mark P. Watson

[57] ABSTRACT

A pulse counter is provided in which the value displayed for the detected value is highly reliable. An SN condition detecting means detects the SN condition of a pulse wave signal (step S201). The SN condition detecting means then determines whether or not the detected SN condition is good based on a specific threshold value (step S202). When a determination is made that the SN condition is good, a display control signal to display the pulse rate on a display means is output to a display method switching means (step S203). Conversely, when a determination is made in step S202 that the SN condition is not good, the pulse rate is not displayed on the display means, but rather a display control signal indicating that no information at all be displayed is output to the display method switching means (step S204).

16 Claims, 10 Drawing Sheets

| PITCH | ~96 | 97~120 | 121~160 | 160~240 |
|---|---|---|---|---|
| × | 16 | 13 | 10 | 7 |

PULSE COUNTER AND PULSE DISPLAY METHOD

TECHNICAL FIELD

The present invention relates to a pulse counter for monitoring the amount of exercise performed by a user and the user's physical condition, and more specifically, to a pulse counter which measures the pulse rate with a high degree of accuracy regardless of whether the user is at rest or exercising.

BACKGROUND OF THE INVENTION

If an individual is able to measure his pulse rate while jogging or running a marathon, for example, then he is able to monitor the amount of exercise performed as well as his physical condition (i.e., to avoid placing himself at risk). Accordingly, for this purpose, a portable pulse counter which can measure the user's pulse rate by being affixed to his arm is proposed. This type of portable pulse counter employs a photoelectric sensor to measure the pulse signal. The pulse rate is then determined by extracting the signal corresponding to the pulse from the pulse wave signal. However, a pulse wave signal obtained while the user is jogging includes a signal component generated by the user's body motion. Accordingly, it is not possible to extract the signal corresponding to the pulse without some correction for the body motion signal.

FIG. 12 is a block diagram showing an example of a conventional pulse counter disclosed in Japanese Patent Application First Publication No. Sho 60-259239. In addition to having a pulse wave detecting sensor 101, this pulse counter has a body motion detecting sensor 1003. The signals obtained from both of these sensors are subjected to frequency analysis at frequency analyzer 1002.

As shown in FIG. 13A, frequency analyzer 1002 converts the pulse wave signal detected by pulse wave detecting sensor 1001 to the spectrum expressed by waveform m. As shown in FIG. 13B, frequency analyzer 1002 converts the body motion signal detected by body motion detecting sensor 1003 to the spectrum expressed by waveform n. Here, waveform n is the result obtained after frequency analysis of the signal detected by body motion detecting sensor 1003. Accordingly, peak value B' expressing the fundamental wave component thereof represents the fundamental frequency of the body's oscillation. Thus, if the frequency of peak B' and the frequency of peak B in waveform m coincide, then the peak value B in waveform m is deemed to be the waveform due to the body's oscillation. The peak obtained by excluding peak value B from waveform m, i.e., peak A, the waveform corresponding to the pulse wave, can be read out.

FIG. 14 is a functional block diagram showing the structure of another conventional pulse counter. Pulse wave sensor 1201 detects the pulse wave in the body, and outputs the detected pulse wave signal to pulse wave signal amplifying circuit 1203. Body motion sensor 1202 detects body motion, and outputs the detected body motion signal to body motion signal amplifying circuit 1204.

Pulse wave signal amplifying circuit 1203 amplifies the pulse wave signal, and outputs it to A/D converter 1205 and pulse waveform shaping circuit 1206. Body motion signal amplifying circuit 1204 amplifies the body motion signal, and outputs it to A/D converter 1205 and body motion waveform shaping circuit 1207. A/D converter 1205 converts the pulse wave signal and body motion signal from analog to digital and outputs the result to CPU 1208. Pulse waveform shaping circuit 1206 shapes the pulse wave signal, and outputs it to CPU 1208. Body motion waveform shaping circuit 1207 shapes the body motion signal and outputs it to CPU 1208.

FIG. 15 is a flow chart showing the operation of the pulse counter shown in FIG. 14. As shown in the flow chart, the presence or absence of the body motion signal is confirmed, the pulse wave calculating method is switched, and the pulse rate is calculated and displayed. In FIGS. 14 and 15, CPU 1208 confirms whether or not a body motion signal is present based on the signal output from body motion waveform shaping circuit 1207, and switches the calculating method (step S1302). During the time that the body motion signal is being confirmed, the pulse wave signal and the body motion signal, which were converted from analog to digital signals (step S1303 and step S1304, respectively), are subjected to a fast Fourier transform (FFT hereinafter) (step S1305), and the pulse wave frequency component is extracted (step S1306).

When a body motion signal cannot be confirmed, the pulse wave is detected (step S1307), and the pulse waveform is subjected to rectangular wave conversion processing (step S1309). During this interval, CPU 1208 once again confirms whether or not body motion was present (step S1308). When body motion is not present, then the pulse rate is calculated from the rectangular wave without modification (step S1310). Because A/D conversion of the pulse wave and body motion are not necessary in this case, operation of A/D converting circuit 1205 is halted, as is the operation of multiplier 1210, which is required for FFT processing. Processing in CPU 1208 necessary for extracting the pulse wave is also halted. Thus, total consumption of electrical power can be reduced.

When body motion is present in step S1308, frequency analysis is performed using FFT processing (step S1305), and the pulse rate is calculated from the extracted pulse wave component (step S1310).

An exercise pitch measurer can also be formed having the same structure as the pulse counter shown in FIGS. 14 and 15. The frequency component of the exercise pitch is specified by body motion waveform shaping circuit 1207. This exercise pitch measurer can be used to inform the user of his running pitch, which is useful information for a runner. In addition, the distance of running can also be obtained from the running pitch and the stride length. An exercise pitch measurer and a pulse counter such as shown in FIGS. 14 and 15 have been disclosed in Japanese Patent Application First Publication No. Hei 7-227383, for example.

However, in the above-described conventional pulse counters, when a body motion signal is present such as shown in FIGS. 14 and 15 (steps S1302, S1308), then body motion detection is carried out all the time, and pulse wave component extraction processing (step S1306) to exclude the body motion spectrum from the pulse wave spectrum, and body motion pitch display (step S1407) are carried out. As a result, a body motion pitch is displayed even during exercise which does not have a periodicity, such as in the case of gymnastics. Moreover, conventional pulse counters perform pulse wave component extraction processing (step S1306) and display the body motion pitch (step S1407) regardless of whether or not noise is present in the detected body motion signal. As a result, an incorrect value may be detected for the body motion pitch, so that the body motion pitch and pulse rate displayed are less reliable.

In addition, conventional pulse counters perform the display of the pulse rate based on the pulse wave signal which is being detected at all times, irrespective of whether or not noise is present in the detected pulse wave signal (step S1303). Accordingly, when the user performs an irregular action, such as sudden action of the hand, the noise component in the spectrum of the pulse wave detection signal increases, increasing the probability of incorrect detection of the pulse rate. Thus, the reliability of the displayed value for the pulse rate falls.

SUMMARY OF THE INVENTION

The present invention was conceived in consideration of the aforementioned circumstances, and has as its objective the provision of a pulse counter in which the displayed value for detected results is highly reliable.

In order to resolve the aforementioned problems, the present invention is provided with a first calculating means for carrying out frequency analysis of the pulse wave signal detected by the pulse wave detecting means; a second calculating means for carrying out frequency analysis of the body motion signal detected by the body motion detecting means; a pulse wave extracting means for calculating the pulse rate by extracting the frequency of the pulse based on the results of frequency analysis by the first and second calculating means; a display means for displaying various information including at least the output of the pulse wave extracting means; a SN condition detecting means for determining whether or not a noise component exceeding a specific value is included in at least one of the results obtained from frequency analysis by the first calculating means and frequency analysis by the second calculating means; and a display method switching means for switching the display details in the display means in response to results detected by the SN condition detecting means.

BEST MODE FOR CARRYING OUT THE INVENTION

Preferred embodiments of the present invention will now be explained with reference to the figures.

A: Structure of the Embodiment

Figure 1:
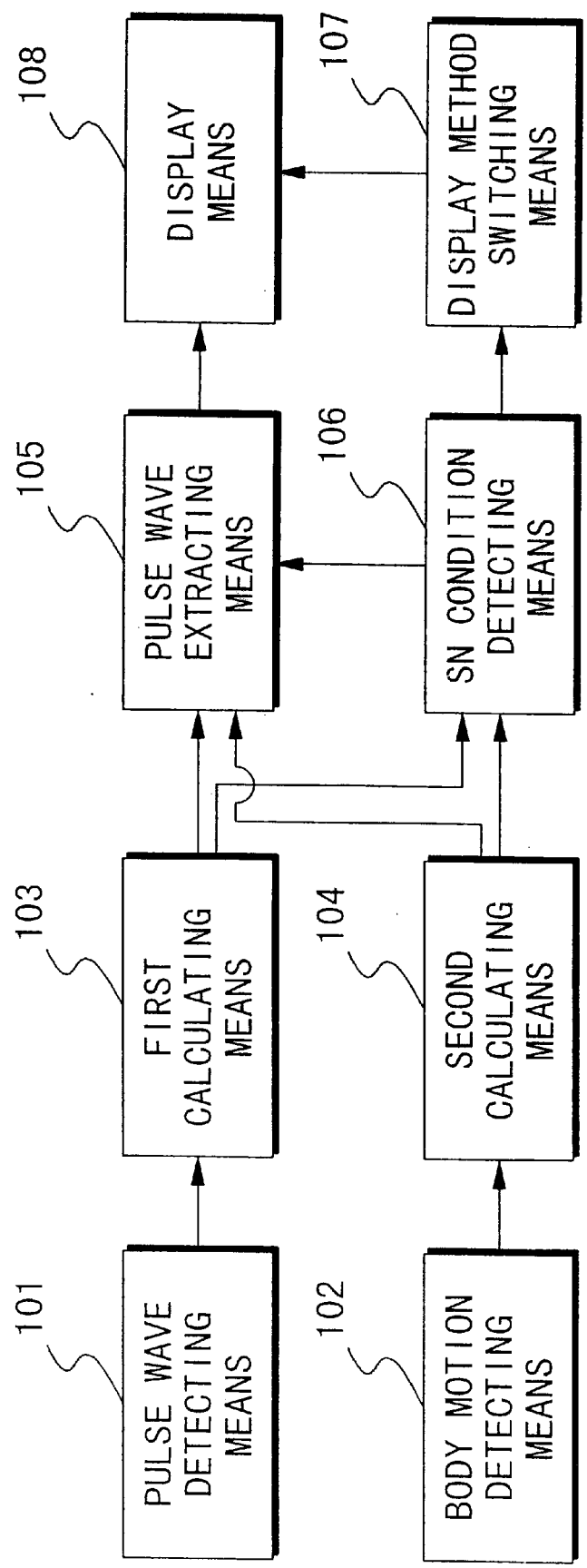
FIG. 1 is a block diagram showing the structure of the pulse counter according to one embodiment of the present invention.

FIG. 1 is a functional block diagram showing one example of a representative structure of the present invention. The pulse wave detecting means 101 detects the pulse wave in the user's body, and outputs the detected pulse wave signal to the first calculating means 103. A piezoelectric microphone, photoelectric sensor or the like may be employed as pulse wave detecting means 101. When a pulse wave detecting means 101 comprising an LED or photo transistor is employed, for example, light radiated by the LED is reflected by the blood in the user's blood vessels, and the reflected light is then received by the photo transistor. Because the hemoglobin in blood absorbs light, the amount of light reflected is a function of the blood capacity flowing through the user's blood vessels.

Thus, the pulse wave is detected by detecting the change in the amount of light reflected by phototransistor. Body motion detecting means 102 detects body motion, and outputs the detected body motion signal to second calculating means 104. An acceleration sensor or the like may be employed for the body motion detecting means, for example. Body motion is detected by attaching this acceleration sensor to the user's arm, for example. First calculating means 103 performs frequency analysis on the signal output from pulse wave detecting means 101, and second calculating means 104 performs frequency analysis on the signal output from body motion detecting means 102. The frequency analysis by first and second calculating means 103,104 may employ FFT, for example.

Pulse wave extracting means 105 specifies the pulse wave component corresponding to the frequency of the pulse from the output of first calculating means 103 and second calculating means 104, i.e., from the results of frequency analysis of the respective outputs from pulse wave detecting means 101 and body motion detecting means 102. In addition, pulse wave extracting means 105 calculates the pulse rate per one-minute time interval from the specified pulse wave component. Display means 108 displays the pulse rate calculated by pulse wave extracting means 105.

Based on the output of first calculating means 103 and the results of frequency analysis by second calculating means 104, SN (Signal/Noise) condition detecting means 106 outputs a display control signal to display method switching means 107 for switching the contents of the display shown on display means 108. Display method switching means 107 switches the contents of the display on display means 108 based on the display control signal output by SN condition detecting means 106. For example, SN condition detecting means 106 detects the SN condition of the body motion signal and the pulse wave signal detected from the result of frequency analysis by first and second calculating means 103,104. When the SN condition is poor, then the pulse rate and body motion pitch are not displayed on display means 108. Conversely, when the SN condition is good, then SN condition detecting means 106 directs the display of the body motion pitch and pulse rate on display means 108.

Figure 2:
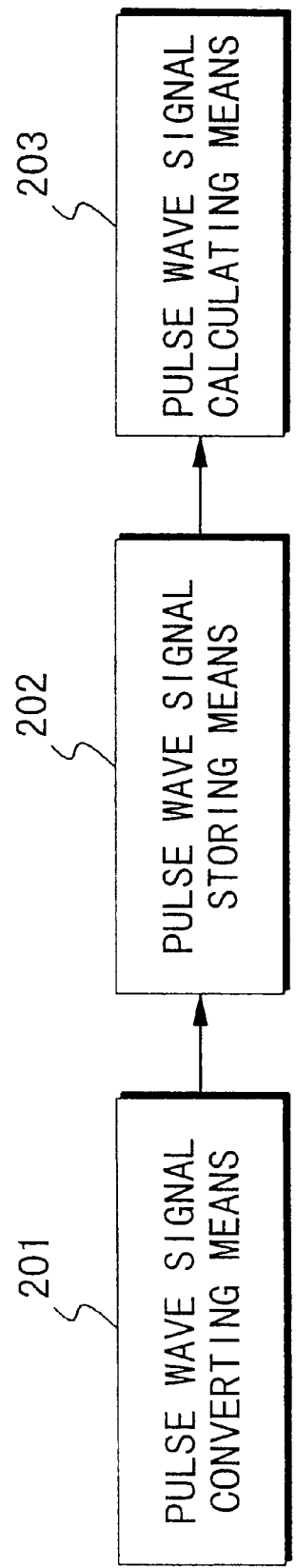
FIG. 2 is a block diagram showing the details of the first calculating means in FIG. 1.

FIG. 2 is a block diagram showing the details of first calculating means 103 shown in FIG. 1. Pulse wave signal converting means 201 converts the body's pulse wave analogue voltage signal detected by pulse wave detecting means 101 to a digital signal, and outputs this result to pulse wave signal storing means 202. Pulse wave signal storing means 202 stores the digitally converted pulse wave signal. Pulse wave signal calculating means 203 sequentially reads out the pulse wave signal stored in pulse wave signal storing means 202, performs frequency analysis of the pulse wave signal, and outputs these results to pulse wave extracting means 105 and SN condition detecting means 106.

Figure 3:
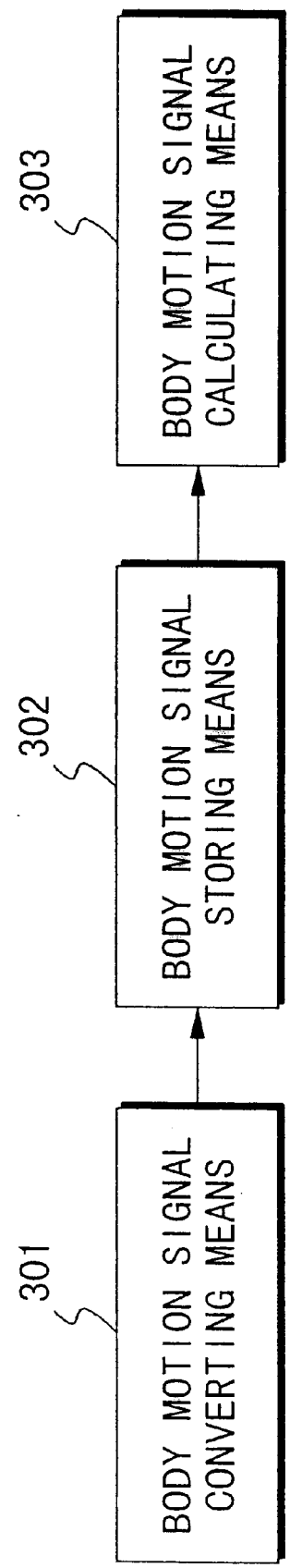
FIG. 3 is a block diagram showing the details of the second calculating means in FIG. 1.

FIG. 3 is a block diagram showing the details of the second calculating means 104 shown in FIG. 1. Body motion signal converting means 301 converts the analogue voltage signal, which was compared to the size of the body motion detected by body motion detecting means 102, to a digital signal, and outputs this result to body motion signal storing means 302. Body motion signal storing means 302 stores the digitally converted body motion signal. Body motion signal calculating means 303 sequentially reads out body motion signals stored in body motion signal storing means 302, performs frequency analysis on the body motion signal, and outputs these results to pulse wave extracting means 105 and SN condition detecting means 106.

B: Operation of the Embodiment (1) Overall Operation

Figure 5:
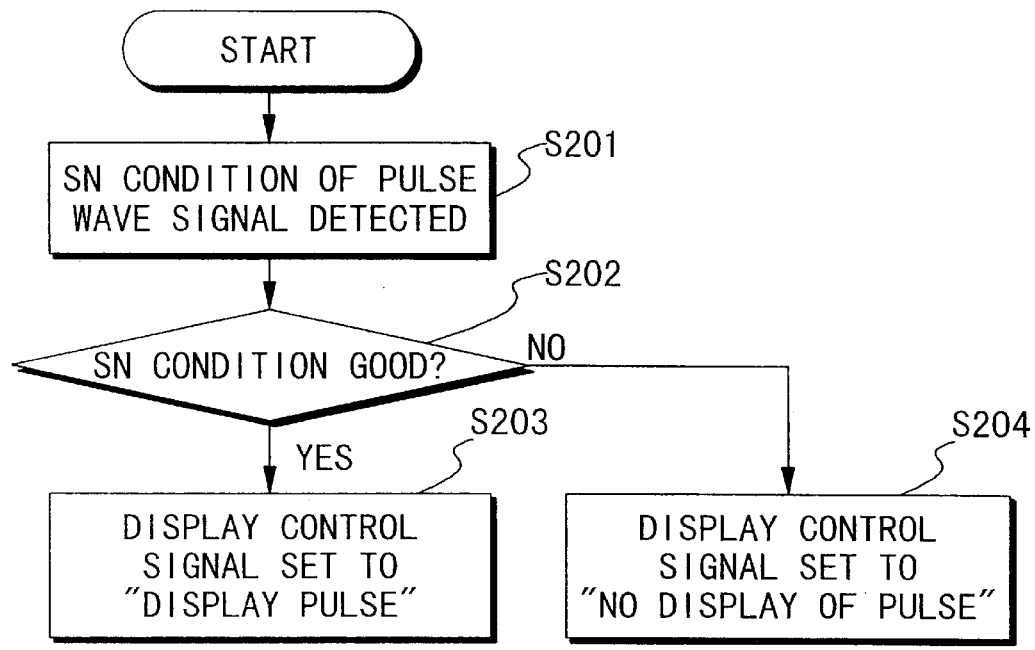
FIG. 5 is a flow chart showing the operation of the SN condition detecting means in FIG. 1.

FIG. 5 is a flow chart showing the operation of SN condition detecting means 106, which is one characteristic feature of the present invention. First, SN condition detecting means 106 detects the SN condition of the pulse wave signal detected by pulse wave detecting means 101 based on the output from first calculating means 103 (step S201). "SN condition" as employed here means the amount of noise included in the detected signal. The method for detecting the SN condition will now be explained in detail.

Figure 7:
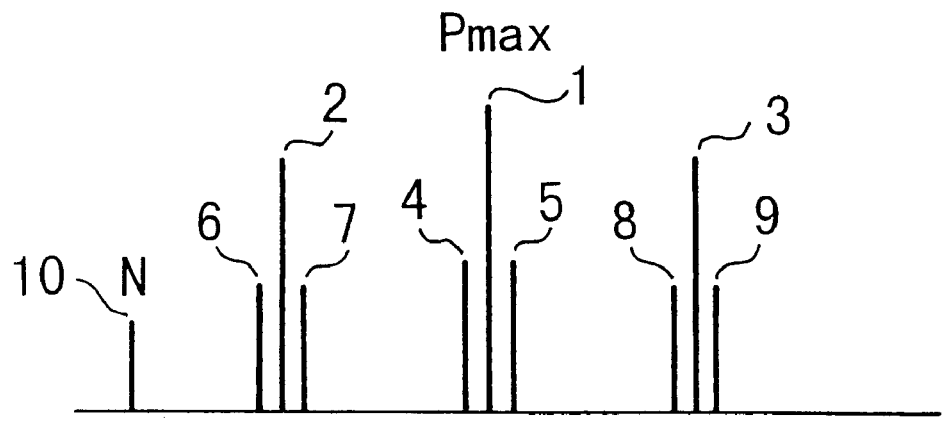
FIG. 7 is an explanatory figure showing the method for specifying the noise base line spectrum N from the body motion signal spectrum.

FIG. 7 is an example of the spectrum for the body motion signal detected by body motion detecting means 102, which is obtained when second calculating means 104 performs a FFT on the pulse wave signal. For example, from among the various base line spectrums, the base line spectrum N which is the tenth largest spectrum as counted from maximum base line spectrum Pmax is designated to represent the base line spectrum of the noise component. The reason for selecting the tenth largest base line spectrum N to represent the base line spectrum of the noise component is that in experiments conducted thus far, the tenth base line spectrum has had the highest probability of being noise. Further, a determination can be made as to whether the SN condition is good or poor by comparing the size of maximum base line spectrum Pmax and the size of base line spectrum N. For example, when the value of N/Pmax is larger than a specific threshold value, then a determination is made that the SN condition is poor. Here, N indicates the size of base line spectrum N, while Pmax indicates the size of base line spectrum Pmax. Note that while the base line spectrum N which is tenth largest in size as counted from maximum base line spectrum Pmax was designated to represent the base line spectrum of the noise component in the preceding example, the present invention is not limited thereto. For example, other base line spectrums, i.e., the seventh base line spectrum for example, may be employed to represent the noise component.

Thus, in this embodiment, the base line spectrums are aligned in order of size, and the base line spectrum at a specific position x from the maximum base line spectrum is determined to be the base line spectrum N of the noise component. The SN condition can be judged by comparing the size of the maximum base line spectrum (which is regarded as the signal component) and the size of the base line spectrum of the noise component. As a result, it is possible to quickly and easily detect the SN condition.

SN condition detecting means 106 determines whether or not the detected SN condition is good based on a specific threshold value (step S202). When a determination is made that the SN condition is good, the display control signal for displaying the pulse rate on display means 108 is output to display method switching means 107 (step S203).

Conversely, when a determination is made in step S202 that the SN condition is not good, then the pulse rate is not displayed on display means 108, and a display control signal indicating that no information at all should be displayed is output to display method switching means 107 (step S204). Note that in step S204, it is also acceptable that SN condition detecting means 106 output a display control signal that directs a blinking display of the pulse rate extracted and calculated by pulse wave extracting means 105. In addition, in step S204, it is also acceptable for SN condition detecting means 106 to output a display control signal for displaying the pulse rate extracted and calculated by pulse wave extracting means 105, and for displaying an indication that the likelihood of error in that display is high. The reason why the pulse rate is not displayed constantly when the SN condition is poor is because it is not possible for pulse wave extracting means 105 to accurately extract the pulse wave component in the presence of a poor SN condition, making the calculation and display of an accurate pulse rate difficult.

Accordingly, in the pulse counter of the present invention, when the SN condition of the detected signal of the pulse wave is poor, i.e., when a great deal of noise is included in the detected signal, then the pulse rate is not constantly displayed. Conversely, when there is a little noise in the signal, the pulse rate is displayed at all times. As a result, the reliability of the displayed value for the pulse rate is improved.

C: Other Methods for Detecting SN Condition (1) First Detecting Method

Figure 8:
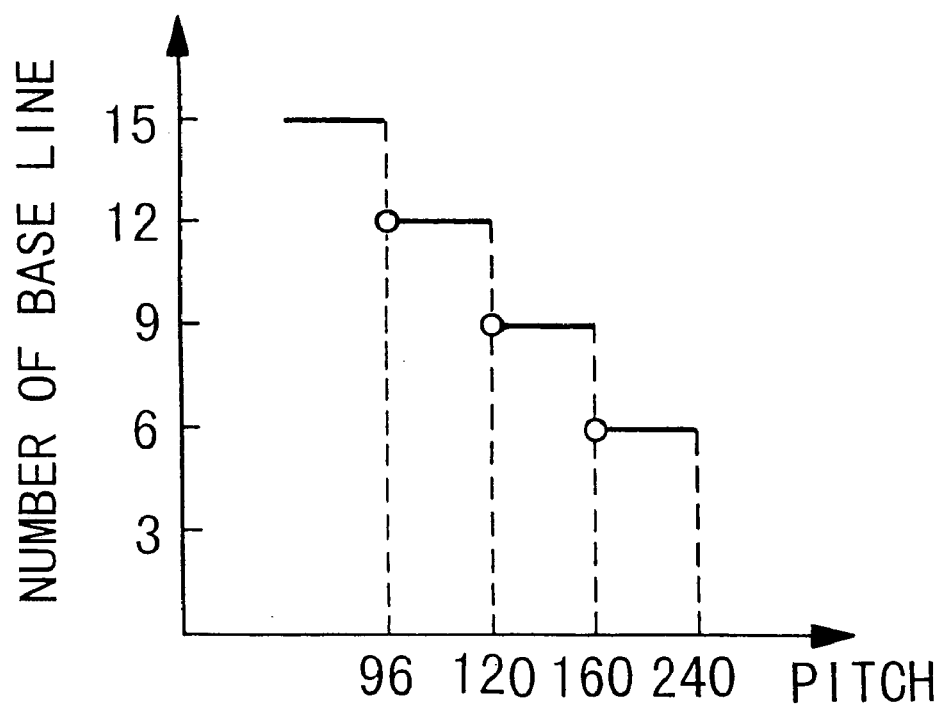
FIG. 8 is an explanatory figure showing the relationship between the body motion pitch number and the number of the base line spectrum in the body motion waveform spectrum thereof.

Modifications of the above-described method for detecting the SN condition will now be explained. FIG. 8 is an explanatory figure showing the relationship between the body motion pitch number and the number of the base line spectrum of the body motion waveform spectrum thereof, in the case where there is no noise included in the body motion waveform detected by body motion detecting means 102, and provided that, in addition to a side lobe component, three base lines are present for the fundamental wave component of body motion, or for one high frequency component. FIG. 7 is an explanatory figure showing the relationship between the body motion pitch number and the xth largest base line spectrum which has been designated to represent the noise component.

In this embodiment, the base line spectrum N of the noise component in FIG. 7 is specified in response to the body motion pitch number calculated by second calculating means 104. In FIG. 8, the body motion pitch number is plotted along the horizontal axis, and the number of the base line spectrum in the body motion waveform spectrum when noise is not included in the body motion waveform is shown along the vertical axis. As shown in this figure, 15 base line spectrums are generated when the body motion pitch number is 96 times or less. When the body motion pitch number is greater than 96 times but less than 120 times, then 12 base line spectrums are generated.

When the number of base line spectrums included in the body motion spectrum obtained by FFT processing by second calculating means 104 is greater than the number of the base line spectrum derived from FIG. 8, then a determination is made that noise in an amount corresponding to the additional number of base line spectrums is present. For example, when the body motion pitch number is 96 times or less, then the fifteen largest base line spectrums are deemed to the base line spectrums of the body motion component, while base line spectrum from the sixteenth largest and beyond are determined to be the noise component.

Figures 9, 10:
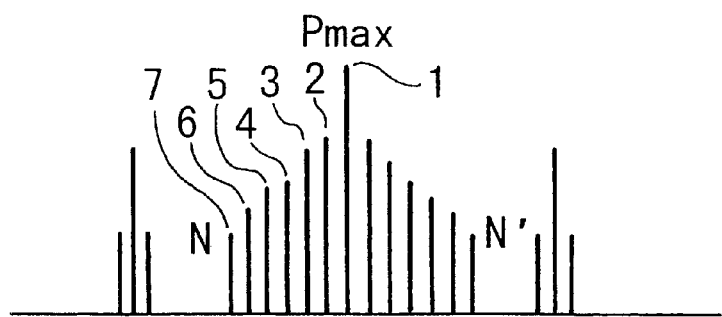
FIG. 9 is an explanatory figure showing a specific example of the noise base line spectrum in response to the pitch number.
FIG. 10 is an explanatory figure showing an alternative method for specifying the noise base line spectrum N from the body motion signal spectrum.

Further, as shown in FIG. 9, the value obtained by adding 1 to the number of the base line spectrum obtained from the relationship between the number of the base line spectrum of the body motion component and the pitch number shown in FIG. 8 is defined as x. Then, the base line spectrums are aligned in order of size, and the base line spectrum at a specific position x from the maximum base line spectrum is determined to be the base line spectrum N of the noise component. The SN condition can be judged by comparing the size of the maximum base line spectrum Pmax and the size of the base line spectrum N. For example, when the value of N/Pmax is larger than a specific threshold value, a determination is made that the SN condition is poor.

Because the base line spectrum N representing the noise component in response to the pitch number of the detected body motion changes in this SN condition detecting method, it is possible to more accurately specify the size of the noise component. Accordingly, the reliability of the pulse rate and body motion pitch displays on display means 108 is improved.

Figure 6:
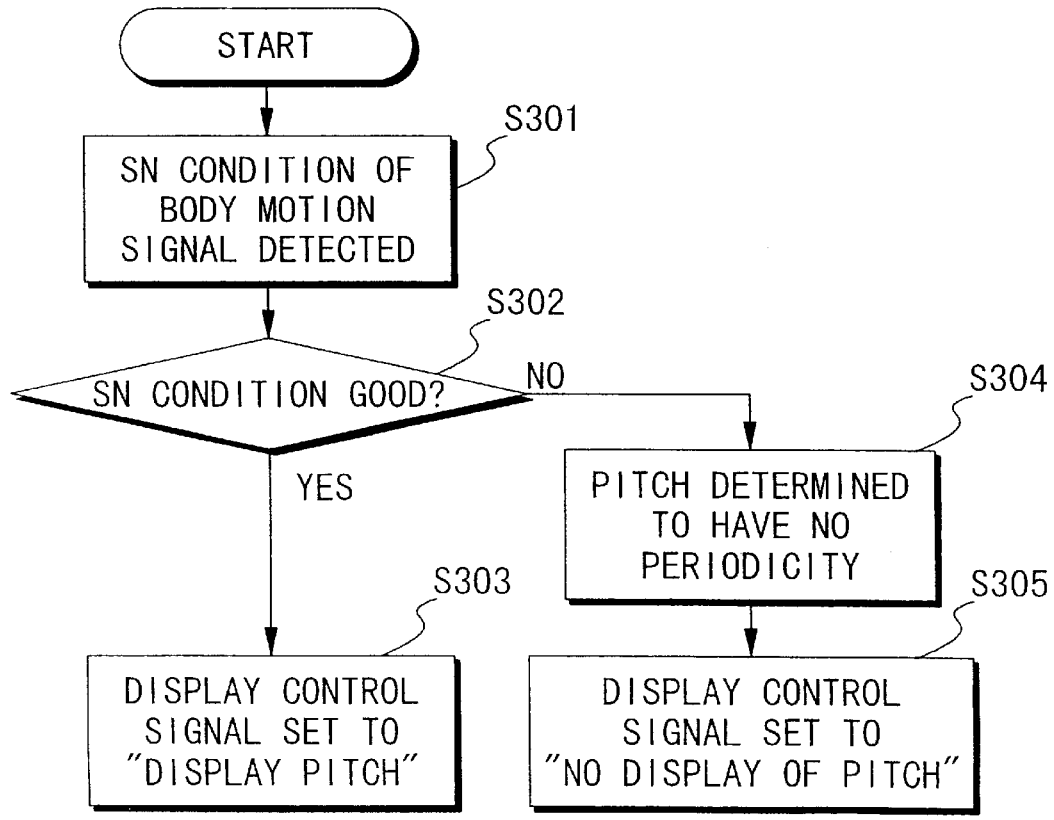
FIG. 6 is a flow chart showing another operation of the SN condition detecting means in FIG. 1.

FIG. 6 is a flow chart showing another operation of SN condition detecting means 106, which is a characteristic feature of this embodiment. First, SN condition detecting means 106 detects the SN condition of the body motion signal detected by body motion detecting means 102 based on the output from second calculating means 104 (step S301). Then, SN condition detecting means 106 determines whether or not the detected SN condition is good based on a specific threshold value (step S302). When a determination is made that the SN condition is good, a display control signal to display the body motion pitch on display means 108 is output to display method switching means 107 (step S303). Here, "body motion pitch" indicates the number of regular body movements that are generated while the user is running, etc. during a one minute interval of time.

Conversely, when a determination is made that the SN condition is not good in step S302, then a determination is made that the detected body motion signal does not have a periodicity (step S304), the body motion pitch is not displayed on the display means 108, and a display control signal directing that no information be displayed is output to display method switching means 107 (step S305). Note that it is also acceptable for SN condition detecting means 106 to output a display control signal for a blinking display of the body motion pitch calculated by pulse wave extracting means 105 in step S305. SN condition detecting means 106 may also output a display control signal for displaying the pulse rate calculated by pulse wave extracting means 105, and for displaying an indication that the probability of an error in that display is high. The reason for not displaying the body motion pitch constantly when the SN condition is poor is that it is not possible for pulse wave extracting means 105 to accurately calculate the body motion pitch when a poor SN condition is present, so that the display of an accurate body motion pitch is difficult.

As a result, in this embodiment, when the SN condition of the detected signal for body motion is poor, i.e., when a great deal of noise is included in the detected signal, then the body motion pitch is not displayed. Conversely, when there is a little noise in the signal, the body motion pitch is displayed at all times. As a result, the reliability of the value displayed for the body motion pitch is improved.

(2) Second Detecting Method

Next, another SN condition detecting method for use in SN condition detecting means 106 will be explained. In this detecting method, the method for specifying the base line spectrum N which is regarded to represent the noise component differs from the above-described first detecting method.

FIG. 10 shows an example of the body motion signal spectrum detected by body motion detecting means 102. This body motion signal spectrum is obtained by FFT processing of the pulse wave signal by second calculating means 104. For example, the various base line spectrums are distinguished between so that the position of the maximum base line spectrum Pmax is designated as the standard, the base line spectrum positioned next to base line spectrum Pmax is designated as the second base line spectrum, and the base line spectrum positioned next to the second base line spectrum is designated as the third base line spectrum. The base line spectrum which is in the seventh position from base line spectrum Pmax, for example, is designated as base line spectrum N representing the noise component. When base line spectrum Pmax is taken as the standard, then there are two base line spectrums N and N' for the base line spectrum on the left side of the figure and on the right side of the figure. One of these base line spectrums is designated as the representative spectrum for the noise component.

Next, a determination of whether or not the SN condition is good is made by comparing the size of maximum base line spectrum Pmax and the size of base line spectrum N (or base line spectrum N'). For example, when the value of N/Pmax is larger than a specific threshold value, the SN condition is judged to be poor. Alternatively, when the value of N'/Pmax is larger than a specific threshold value, then a determination may be made that the SN condition is poor.

As a result, because the base line spectrum which is separated from the maximum base line spectrum Pmax by a specific spectrum number only is designated to represent the noise component in this SN detecting method, it is possible to specify the size of the noise component more quickly and easily, thus improving the reliability of the display of the body motion pitch and pulse rate on display means 108.

(3) Third Detecting Method

In the above-described SN condition detecting method, one of either the base line spectrum N or the base line spectrum N' which are present on either side of the maximum base line spectrum Pmax is designated to represent the noise component. However, the present invention is not limited thereto. For example, it is also acceptable to designate the average of the sizes of base line spectrum N and base line spectrum N' as a value representing the noise component.

For example, when the value of $\{(N+N')/2\}/Pmax$ exceeds a specific threshold value, a determination is made that the SN condition is poor. Here, N and N' indicate the size of base line spectrum N and base line spectrum N', respectively. Pmax indicates the size of base line spectrum Pmax.

The reason for designating the average value of the sizes of base line spectrum N and base line spectrum N' as a value representing the noise component is that noise may be present in only one of the base line spectrums. When the noise in that base line spectrum is small, it is possible that the size of this noise component may be incorrectly determined. For this reason, rather than taking the average, the size of the two base line spectrums may be compared, and the larger of the base line spectrums employed to determine the size of the noise component.

As a result, in this SN condition detecting means, the size of the noise component can be judged more accurately, thus further improving the reliability of the pulse rate and body motion pitch display on display means 108.

D: Examples of Specific Applications

Figure 4:
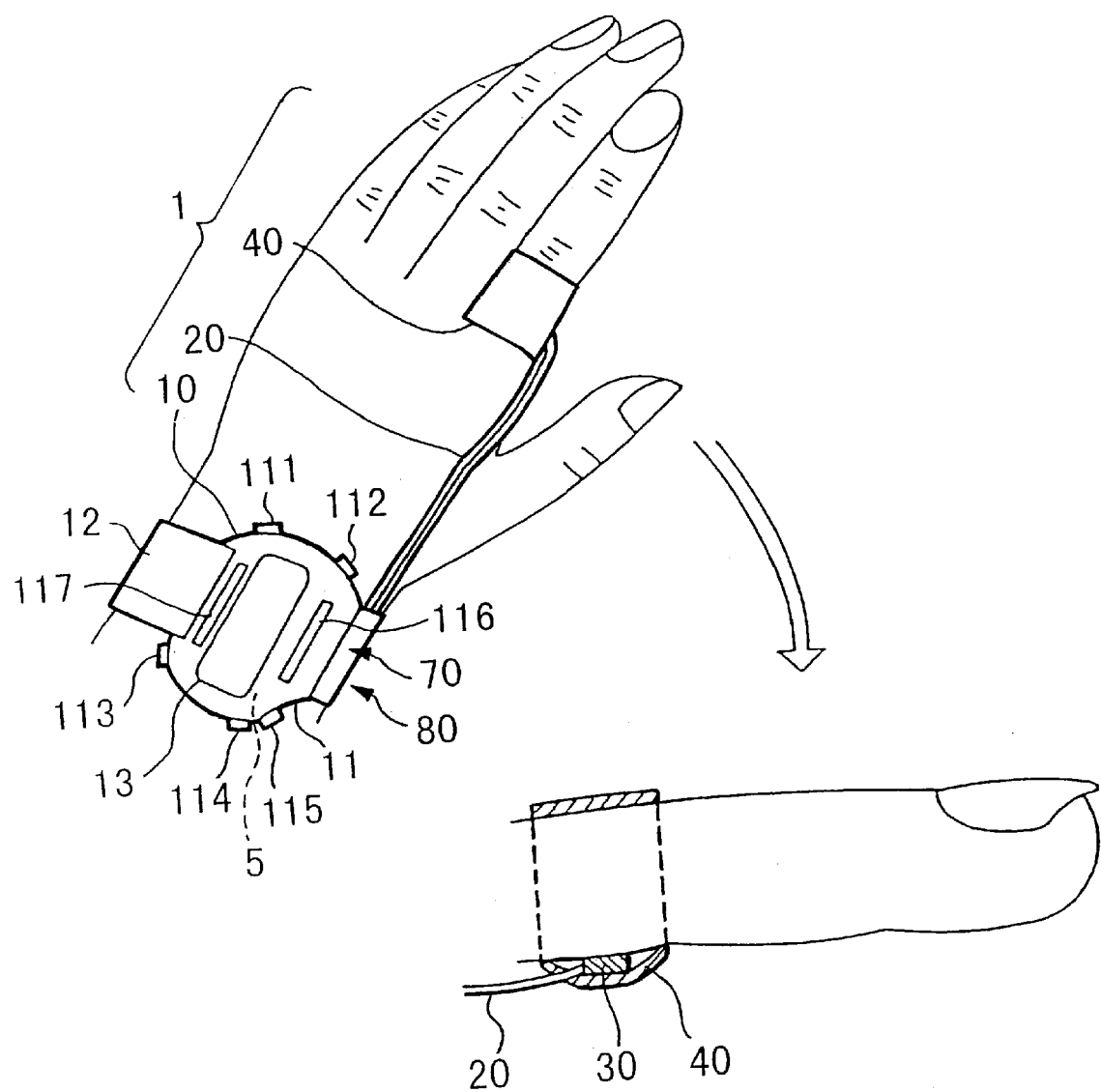
FIG. 4 is an explanatory figure showing an example of the mechanical structure of the pulse counter according to an embodiment of the present invention.

FIG. 4 is a sketch drawing of the case where the pulse counter according to this embodiment is realized as a portable device. In FIG. 4, pulse counter 1 (portable pulse wave measuring device) of this example, is roughly comprised of a device main body 10 having a wristwatch structure, a cable 20 connected to device main body 10, and a sensor unit 30 (pulse wave detecting means) provided to the end of cable 20. A connector piece 80 is formed to the end of cable 20, and attaches in a freely releasable manner to connector member 70 which is formed to the 6 o'clock side of device main body 10. A wristband 12 is attached to device main body 10 which wraps around the user's wrist from the 12 o'clock position and affixes at the 6 o'clock position of the wristwatch. Device main body 10 can be freely attached and removed from the user's wrist by means of this wristband 12. Pulse wave detecting sensor unit 30 is blocked from light by band 40 employed for fixing the sensor in place, and is attached at the base of the user's index finger. By attaching pulse wave detecting sensor unit 30 in this way to the base of the finger, cable 20 can not only be made shorter, but will not present interference to the user during exercise. Additionally, it is known that when the temperature distribution from the palm to the tip of the finger is measured, the temperature at the tip of the finger drops markedly in the case where the temperature of the surrounding environment is low, whereas the temperature at the base of the finger falls comparatively little. Accordingly, if pulse wave detecting sensor unit 30 is attached to the base of the finger, it is possible to accurately measure pulse rate and the like, even in the case where exercising outdoors during cold weather.

Device main body 10 is provided with a watch case 11 (main body case) made of a resin. A liquid crystal display 13 (display means) having an EL back light is provided to the front of watch case 11 for displaying the current time and date, as well as the length of time spent running, the running pitch and pulse wave information such as the pulse rate. Liquid crystal display device 13 may be comprised of segmental or dot display regions. When dot display regions are employed, then the various informations may be graphically displayed.

A body motion detecting sensor 90 which employs an acceleration sensor 91 (body motion detecting means) for detecting body motion as a body motion signal TS is housed inside watch case 11. Watch case 11 also houses a controller comprising a microcomputer or the like which carries out various control functions and data processing for determining the change in the pulse rate based on the pulse wave signal MS measured by pulse wave detecting sensor unit 30, and for displaying this change on liquid crystal display device 13. The controller also includes a watch circuit for displaying the clock time, lap time, split time and the like on liquid crystal display device 13. Button switches 111 to 115 are provided to the outer periphery of watch case 11, to permit external manipulation to switch the display mode or change the time.

E: Modification (1)

In the preceding embodiment, SN condition detecting means 106 detects the SN condition of the pulse wave detecting signal or the body motion detecting signal, and displays the pulse rate or body motion pitch only when the SN condition is good. Accordingly, the reliability of the values displayed is improved. However, the pulse counter of this embodiment even further improves the reliability of the display value.

In addition to the compositional elements of the above-described pulse counter shown in FIG. 1, in this embodiment, the value measured prior to the current point in time, or an average of several values measured immediately preceding the current point in time, is defined as the standard, a specific calculating method is used to set upper and lower limit values based on this standard value, the result of the current measurement is checked to see whether or not it is within the range extending from the lower limit value to the upper limit value (i.e., within the window), and a decision is then made whether or not to display that measured value based on the result of this check. Here, the upper and lower limit values are set based on the SN condition detected by the SN condition detecting means 106 described above.

For example, when the SN condition is poor, i.e., when there is a considerable noise component such that the likelihood of an error in the display value is high, then the range from the lower limit value to the upper limit value (i.e., the width of the window) is made more narrow. When the measured value does not fall within the window, then that value is not displayed by the display means.

Note that when a measured value is obtained which deviates from the window, it is of course also possible to provide an "error" display, so that the user is clearly informed whether or not the displayed value is the true pulse rate or body motion pitch.

In this embodiment, the upper and lower limit values of the window within which an effective measured value is obtained will change based on the SN condition. As a result, it is possible to even further improve the reliability of the value displayed by the display means.

F: Modification (2)

Figure 11:
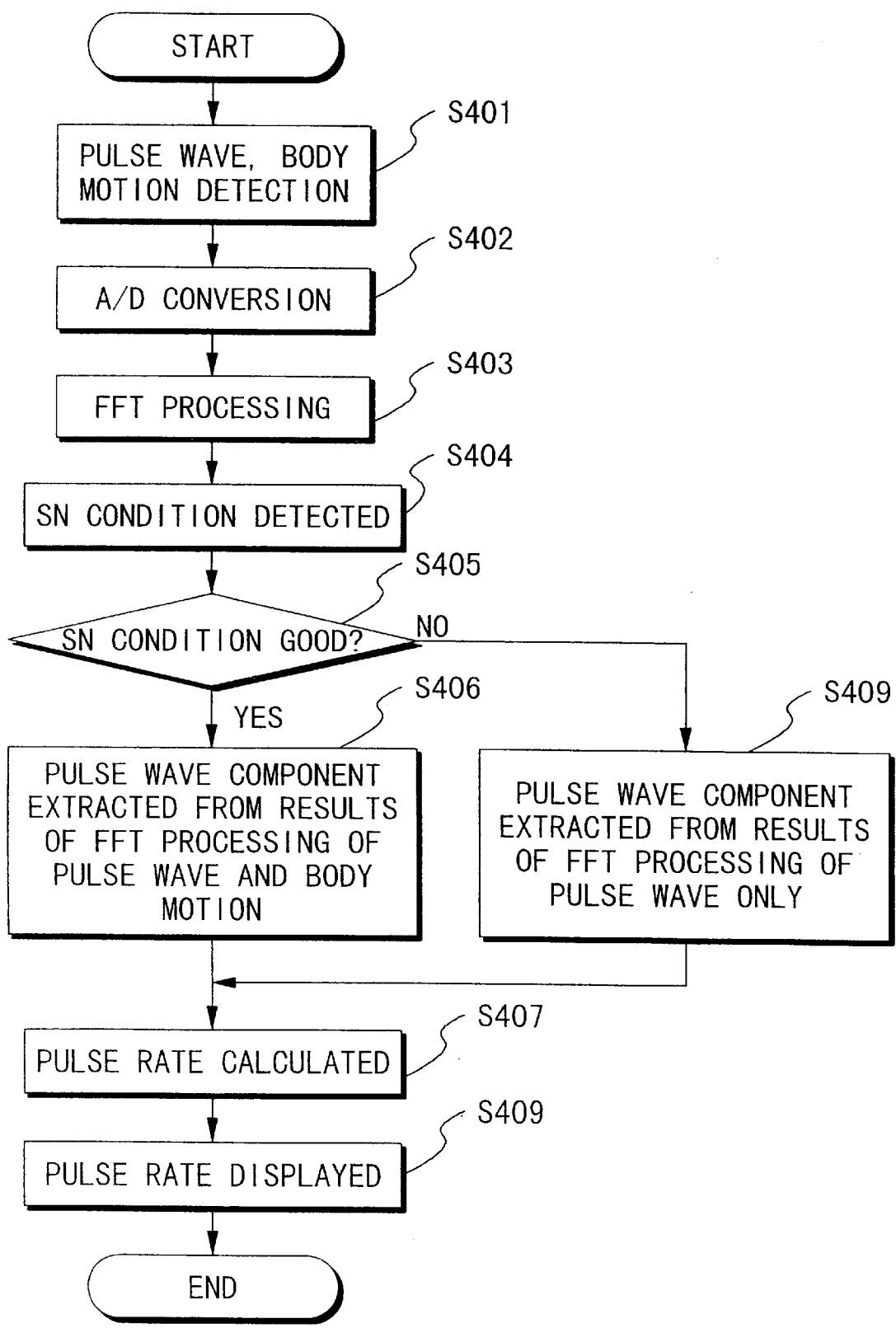
FIG. 11 is a flow chart showing the operation of the pulse counter according to a modification of the present invention.
Figure 12:
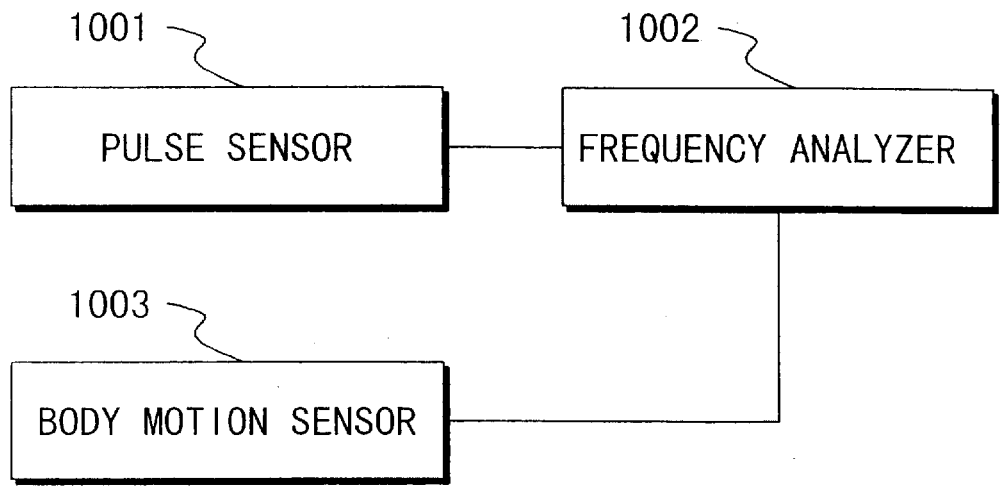
FIG. 12 is a block diagram showing an example of a conventional pulse counter.
Figure 13A:
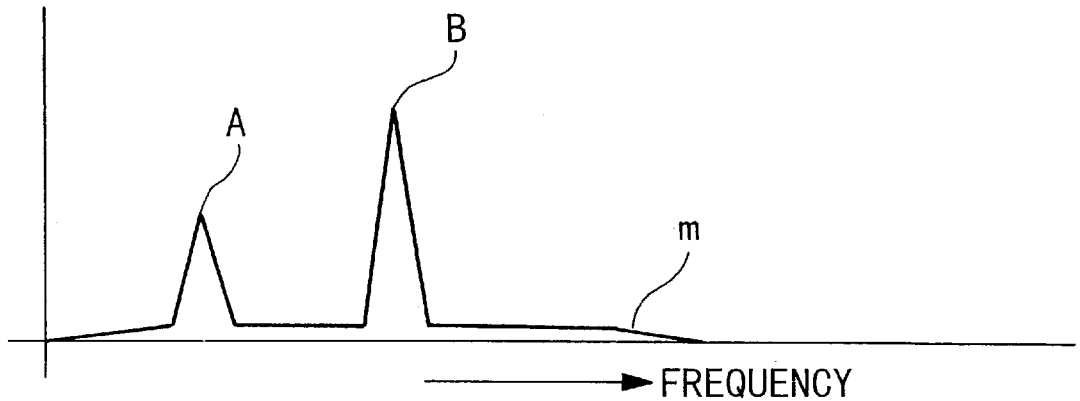
FIG. 13 is an explanatory figure showing an overview of the operation for extracting the pulse wave.
Figure 13B:
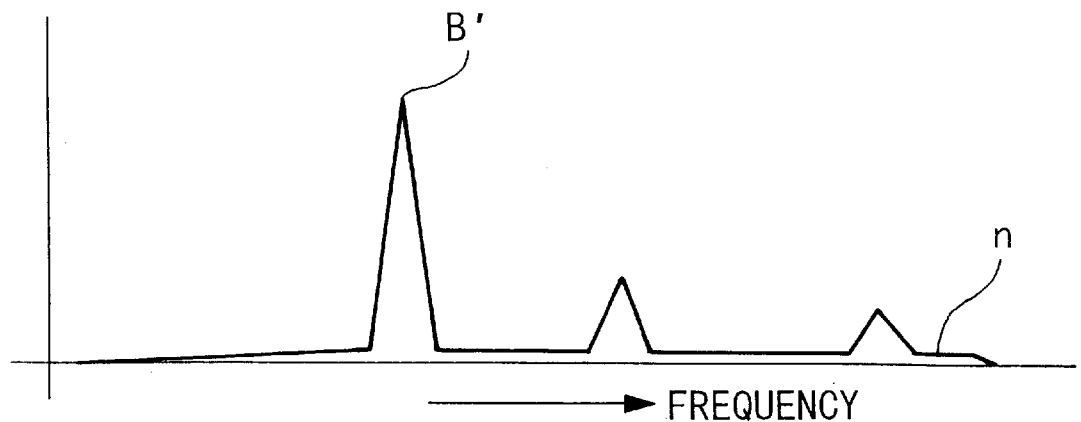
Figure 14:
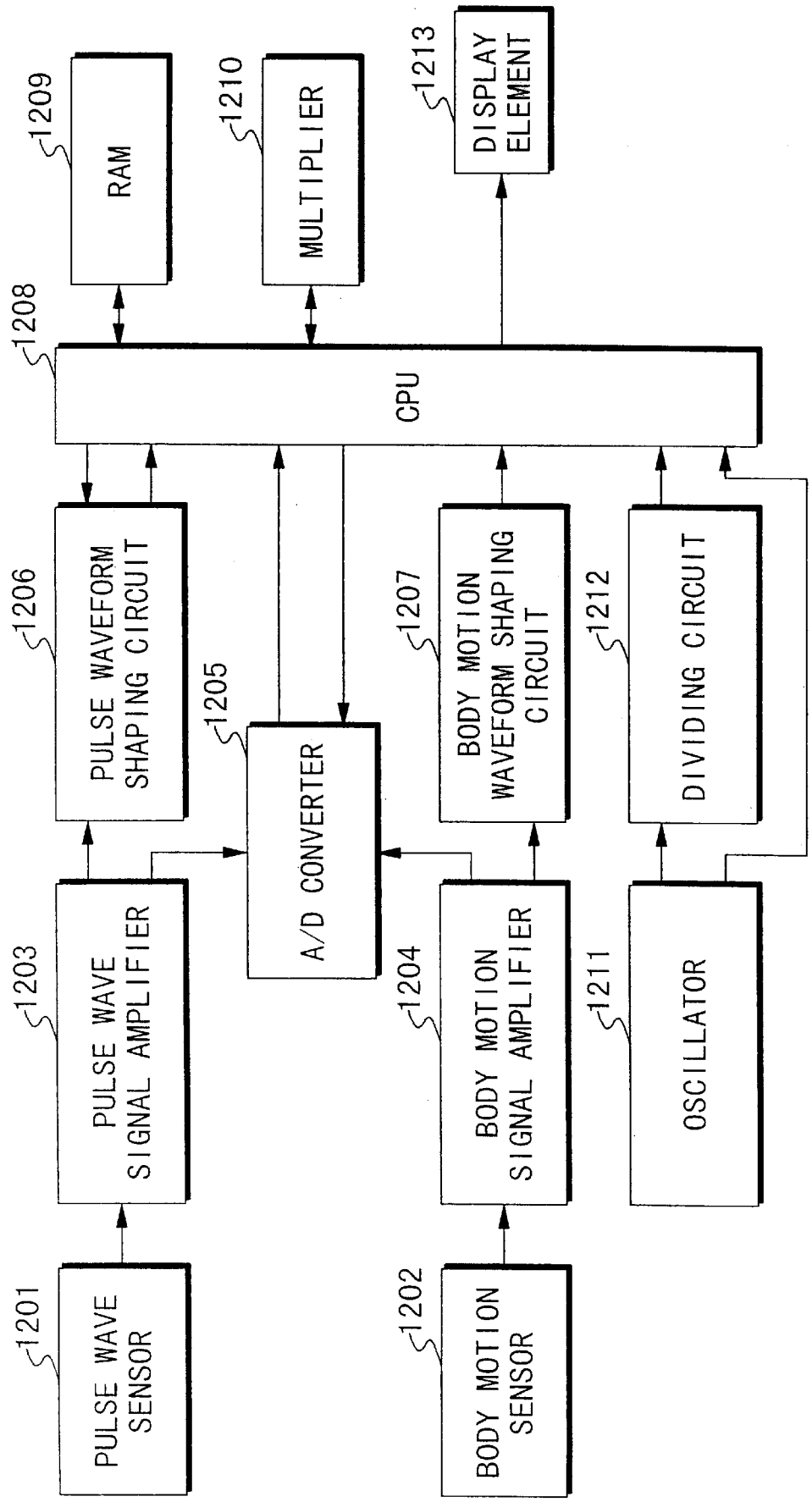
FIG. 14 is a block diagram showing the structure of another conventional pulse counter.
Figure 15:
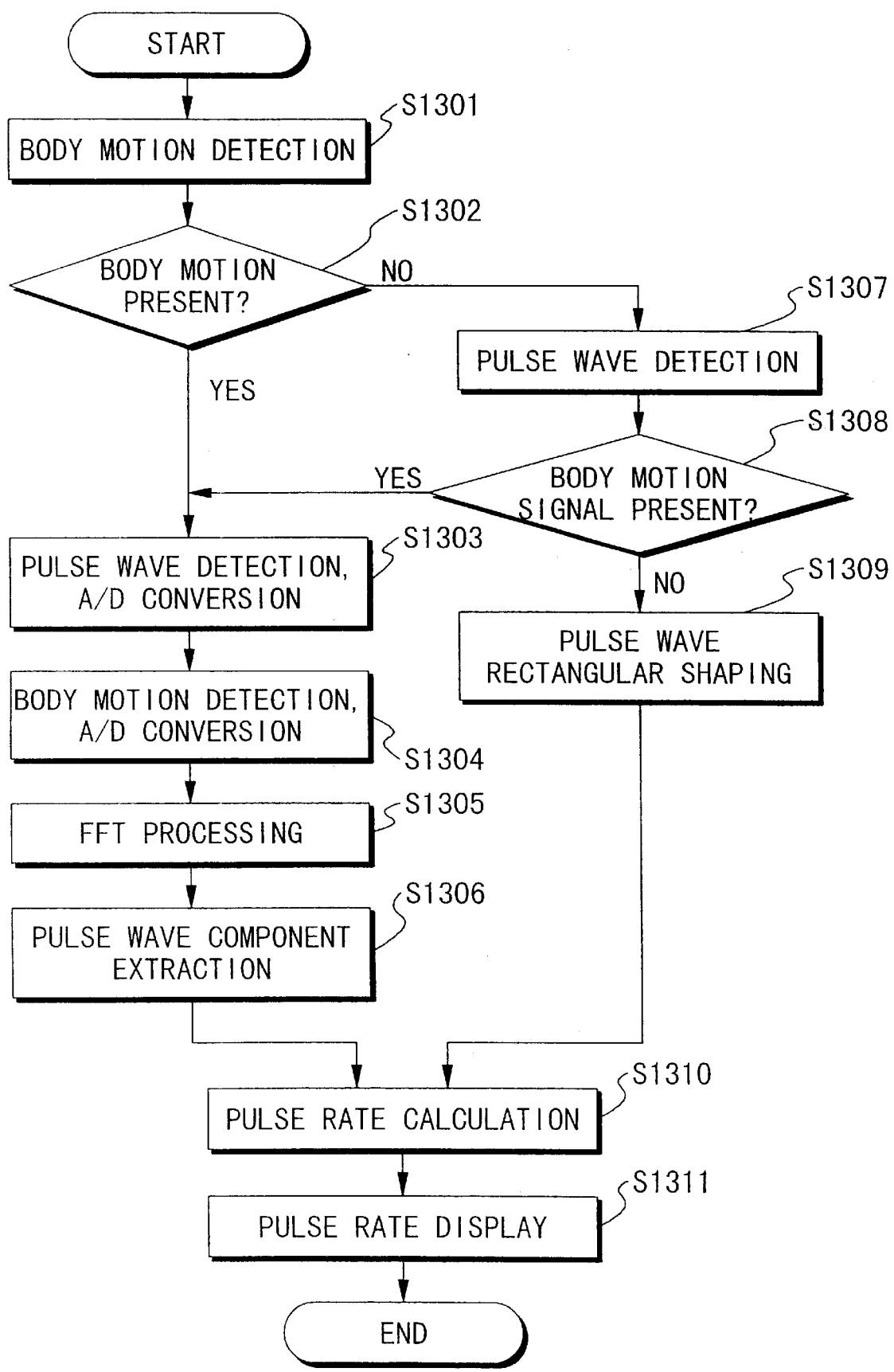
FIG. 15 is a flow chart showing the operation of the pulse counter shown in FIG. 14.

FIG. 11 is a flow chart showing the operation of the pulse counter according to the present modification. As shown in the flow chart, the presence or absence of a body motion signal is confirmed, the method for calculating the pulse wave is switched, and the pulse rate is calculated and displayed. This modification is characterized in that the SN condition detecting means 106 shown in FIG. 1 determines whether or not the SN condition is good in step S402, and the pulse rate calculating method is switched based on the results of that determination. The rest of the design of this modification is that same as that of the pulse counter shown in FIG. 1. Accordingly, the operation of this embodiment will be explained with reference to FIGS. 1 and 11 below.

First, pulse wave detecting means 101 detects the pulse wave and body motion detecting means 102 detects body motion (step S401). The detected pulse wave and body motion signals are converted from analog to digital signals by first and second calculating means 103 and 104, respectively (step S402), and are subjected to FFT processing (step S403). SN condition detecting means 106 detects the SN condition for the FFT processed body motion signal (step S404), and determines whether or not the SN condition is good (step S405).

When SN condition detecting means 106 determines that the SN condition is good in step S405, pulse wave extracting means 105 extracts the frequency component of the pulse wave from the results obtained from FFT processing of the pulse wave and body motion signals (step S406). Then, pulse wave extracting means 105 calculates the pulse rate from the frequency component of the extracted pulse wave (step S407), and displays the calculated pulse rate on display means 108 (step S408).

Conversely, when SN condition detecting means 106 determines that the SN condition is not good in step S405, pulse wave extracting means 105 extracts the frequency component of the pulse wave only from the results obtained from FFT processing of the pulse wave signal (step S409). Pulse wave extracting means 105 then calculates the pulse rate from the frequency component of the extracted pulse wave (step S407), and displays the calculated pulse rate on display means 108 (step S408).

In this way, the body motion waveform is not used to calculate the pulse rate when the SN condition of the body motion waveform is not good. Rather, the pulse rate is calculated using only the pulse waveform. The reason for this is that if the pulse rate is calculated using a signal in which noise is present, then there are numerous errors in the calculation of that pulse rate.

Thus, in the pulse counter according to this modification, the pulse waveform is extracted using the body motion waveform only when the SN condition of the body motion waveform is good such that there is a little noise present therein. As a result, it is possible to more accurately extract the pulse waveform, further improving the reliability of the values displayed on the display means. Further, if a method is employed to narrow the width of the window described in modification (1) above when a determination is made in step S405 that the SN condition is not good, then the reliability of the detected value is improved even more.

Finally, in the preceding example modifications, the method for extracting the pulse waveform changed based on the SN condition of the body motion waveform. However, the present invention is not limited thereto. For example, it is also acceptable to change the method for extracting the pulse waveform based on the SN condition of the body motion waveform and the SN condition of the pulse waveform.

What is claimed is:

1. A pulse counter comprising:
    a first calculating means for carrying out frequency analysis of a pulse wave signal detected by a pulse wave detecting means;
    a second calculating means for carrying out frequency analysis of a body motion signal detected by a body motion detecting means;
    a pulse wave extracting means for calculating the pulse rate by extracting the frequency of the pulse based on the results of frequency analysis by the first and second calculating means;
    a display means for displaying information at least including the output of the pulse wave extracting means;
    a SN condition detecting means for determining whether or not a noise component exceeding a specific value is included in at least one of the results obtained from frequency analysis by the first calculating means and frequency analysis by the second calculating means; and
    a display method switching means for switching display contents in the display means in response to results detected by the SN condition detecting means.

2. A pulse counter according to claim 1, wherein the pulse wave extracting means calculates the pulse rate by extracting the frequency of the pulse based on the results of frequency analysis by the first calculating means and the second calculating means, and calculates the body motion pitch which is a function of the period of the body motion.

3. A pulse counter according to claim 2, wherein the display method switching means does not perform a display on the display means when the SN condition detecting means determines that a noise component exceeding a specific value is included.

4. A pulse counter according to claim 2, wherein the display method switching means carries out a blinking display on the display means when the SN condition detecting means determines that a noise component exceeding a specific value is included.

5. A pulse counter according to claim 2, wherein, when the SN condition detecting means determines that a noise component exceeding a specific value is included, the display method switching means displays the pulse rate or body motion pitch calculated by the pulse wave extracting means, and displays an indication that the probability of an error in the displayed value is high.

6. A pulse counter according to claim 2, wherein the SN condition detecting means determines whether or not a noise component exceeding a specific value is included based on the state of each base line spectrum in the pulse wave signal spectrum.

7. A pulse counter according to claim 2, wherein the SN condition detecting means determines whether or not a noise component exceeding a specific value is included based on the state of each base line spectrum in the body motion signal spectrum.

8. A pulse counter according to claim 2, wherein the SN condition detecting means determines whether or not a noise component in excess of the specific value is included based on whether or not the ratio of the power between the base line spectrum having the maximum power in the pulse wave signal spectrum and the base line spectrum which is deemed to be the base line spectrum of the noise component is greater than a specific threshold value.

9. A pulse counter according to claim 2, wherein the SN condition detecting means determines whether or not a noise component in excess of the specific value is included based on whether or not the ratio of the power between the base line spectrum having the maximum power in the body motion signal spectrum and the base line spectrum which is deemed to be the base line spectrum of the noise component is greater than a specific threshold value.

10. A pulse counter according to claim 9, wherein the SN condition detecting means aligns each of the base line spectrums in order of largest powder, and designates the base line spectrum at a given position from the base line spectrum having the maximum power as the base line spectrum of the noise component.

11. A pulse counter according to claim 9, wherein, in the spectrum, the SN condition detecting means designates the base line spectrum which is located at a position which is separated from the base line spectrum having the maximum power by a given base line spectrum only as the base line spectrum of the noise component.

12. A pulse counter according to any one of claims 1 through 11, wherein:

the SN condition detecting means determines whether or not a noise component which will cause an error in the calculation of the pulse rate is included in at least one of the results of frequency analysis by the first calculating means and frequency analysis by the second calculating means, sets a specific standard value based on the results obtained up through the previous calculation by the pulse wave extracting means; sets upper and lower limits for this standard value based on the results detected by the SN condition detecting means; and determines whether or not the pulse rate or body motion pitch calculated by the pulse wave extracting means is within the window defined by these upper and lower limits; and the display method switching means switches the details of the display on the display means based on the determination of the SN condition detecting means.

13. A pulse counter according to claim 12, wherein, when the SN condition detecting means determines that the pulse rate or body motion pitch are within the window, the display method switching means displays an indication on the display means that the probability of an error in the displayed value is high.

14. A pulse counter according to any one of claims 1 through 11, wherein:

the pulse wave extracting means extracts the pulse wave frequency using either a first extracting method in which the pulse frequency is extracted from the results of frequency analysis by the first calculating means, or a second extracting method in which the pulse frequency is extracted based on both the result of frequency analysis by the first calculating means and the result of frequency analysis by the second calculating means.

15. A pulse counter according to claim 14, wherein, when the SN condition detecting means determines that a noise component which will cause an error in the body motion pitch is included in the results of frequency analysis by the second calculating means, the pulse wave extracting means extracts the pulse wave frequency using the first extracting method.

16. A pulse display method characterized in the provision of:

a first calculating step for performing frequency analysis of a detected pulse wave signal;

a second calculating step for carrying out frequency analysis of a body motion signal detected by a body motion detecting means;

a pulse wave extracting step for extracting the frequency of the pulse based on the results of frequency analysis by the first and second calculating steps, and calculating the pulse rate;

a display step for displaying information including the pulse rate;

a SN condition detecting step for determining whether or not a noise component exceeding a specific value is included in at least one of either the result obtained from frequency analysis in the first calculating step or the result obtained from frequency analysis in the second calculating step; and a display method switching steps for switching display contents in the display step in response to results detected by the SN condition detecting means.

* * * * *

UNITED STATES PATENT AND TRADEMARK OFFICE
CERTIFICATE OF CORRECTION

PATENT NO.   : 6,099,478                                        Page 1 of 1
DATED        : August 8, 2000
INVENTOR(S)  : Ichiro Aoshima, et al.

It is certified that error appears in the above-identified patent and that said Letters Patent is hereby corrected as shown below:

<u>Title page,</u>
Item [75], Inventors: insert -- Chiaki Nakamura, of Chiba, Japan --.

Signed and Sealed this

Twenty-fifth Day of December, 2001

Attest:

JAMES E. ROGAN
*Attesting Officer*          *Director of the United States Patent and Trademark Office*